(12) United States Patent
Iwakawa (10) Patent No.: US 6,316,016 B1
(45) Date of Patent: Nov. 13, 2001

(54) METHOD AND COMPOSITION FOR CREATING A PROTECTIVE BARRIER

(75) Inventor: Toru Iwakawa, Tokyo (JP)

(73) Assignee: Nippon Eisei Center Co., Ltd., Tokyo (JP)

(*) Notice: Subject to any disclaimer, the term of this patent is extended or adjusted under 35 U.S.C. 154(b) by 0 days.

(21) Appl. No.: 09/303,672

(22) Filed: May 3, 1999

Related U.S. Application Data (63) Continuation-in-part of application No. 08/703,473, filed on Aug. 27, 1996, now Pat. No. 5,902,597, which is a continuation of application No. 08/449,337, filed on May 24, 1995, now abandoned.

(51) Int. Cl.[7] ............................. A01N 25/16; A01N 25/08
(52) U.S. Cl. ................. 424/409; 514/945; 424/DIG. 11; 427/426
(58) Field of Search .............................................. 424/409

(56) References Cited

U.S. PATENT DOCUMENTS 5,902,597 * 5/1999 Iwakawa et al. ..................... 424/409

OTHER PUBLICATIONS

M. Higabe "Clean Barreck Method and Its Effects" 1987.*

Enviromental Tech. Management vol. 5, No. 4 pp. 191–198.*

* cited by examiner

Primary Examiner—Peter F. Kulkosky
(74) Attorney, Agent, or Firm—Smith, Gambrell & Russell, LLP (57) ABSTRACT

A method for creating a barrier to protect wood materials for house construction or wooden structures such as houses from humidity, moisture and/or biological attacks, such as wood decaying fungi and termites, is disclosed. The method is to treat wood itself or, preferably, the ground surface under the floor with a liquid containing a synthetic resin emulsion and an anti-fungal and wood preservative agent and/or a pesticide such as termite-controlling agent, and further, a foaming agent. The barrier contains a selected copolymer of vinyl acetate and a polyurethane polymer.

26 Claims, 2 Drawing Sheets

FIG. 2

METHOD AND COMPOSITION FOR CREATING A PROTECTIVE BARRIER

REFERENCE TO RELATED APPLICATION

This application is a continuation-in-part of U.S. patent application Ser. No. 08/703,473 filed Aug. 27, 1996, now U.S. Pat. No. 5,902,597 which in turn is a continuation of U.S. patent application Ser. No. 08/449,337 filed May 24, 1995, now abandoned.

BACKGROUND OF THE INVENTION

The present invention relates to a method and composition for creating a barrier for environmental control and protection. In one aspect of the invention, a barrier is provided for controlling vegetation. In another aspect of the invention, a barrier is provided for protecting concrete from acid attack and deterioration. In a further aspect of the invention, a barrier is provided for the protection of underground or partially underground structures, such as cable, pipelines, and metal or concrete tanks to guard against leakage.

In the landscaping of homes, office parks and golf courses, it is frequently desirable and necessary to control vegetation. For example, there is a need to separate flower beds from grassy areas in order to control invasion of the flower beds by grasses. For golf courses, greens are planted with a different grass than the surrounding area and it would be helpful to prevent invasion by undesirable grass species into the green area. Also, there is a problem with moles burrowing into the green. Therefore, a need exists to control vegetation and/or restrain undesirable vegetation and pests in certain well defined areas.

Furthermore, there exists a need for protecting concrete surfaces from acid-caused effects. The problem of acid rain not only attacks trees but causes problems for concrete also. Acid build-up in the soil can attack or deteriorate concrete structures such as roadways, airport runways, concrete buildings and the like.

This invention also relates to a method and composition for creating a protective barrier to protect various structures against attack by insects, humidity and fungi. More particularly, the present invention relates to compositions and methods to protect wooden structures from termites and other wood-decaying injurious insects.

All types of wooden structures, and in particular wooden houses, are subject to being exposed to the action of humidity in the atmosphere and, depending on location, to dampness or water seepage. This creates an ideal atmosphere for growth of fungi such as mildew and the like. When wooden structures are attacked by wood-decaying fungi, they can be seriously damaged, especially when the foundation that supports the structure and stability of the house is attacked. The deterioration of wooden structures by the action of humidity and by the biological attackers are inter-related, because wood-decaying fungi and termites thrive and proliferate under humid conditions, such as are found under the floors of homes where water evaporates from the ground surface.

It is, therefore, very important to protect the wood materials employed for house construction and wooden houses and structures from the action of humidity, fungi, insects and other biological attacks in one convenient procedure.

Heretofore, proposals have been made to prevent the action of humidity from the ground surface and to control the biological attacks. For example, it has been suggested to cover the ground surface with polyethylene sheets in order to cut off humidity therefrom. Likewise, it has been proposed to cover the ground surface with sheets, called "termite-controlling sheets," in order to attain various objects, such as prevention of exposure to humidity, for wood preservation and for termite control at the same time.

However, these methods have occasioned a number of drawbacks. For instances, it is a labor intensive effort to spread sheets on a ground surface in a satisfactory manner. It is necessary to first cut sheets to adapt them to irregularly shaped foundations; in order to reduce the tendency to cause gaps thereby leading to imperfect prevention against humidity and moisture.

It has also been proposed in the past to spray a variety of synthetic resin-containing liquid preparations, which can contain active ingredients such as termite-controlling agents and/or wood preservative agents, on the ground surface under the wooden structure. However, these methods also were not totally successful. For example, the synthetic resin liquid preparations tend to penetrate into the soil before a dried film is formed on the soil surface. Hence, a much larger quantity of the liquid is required in order to attain the desired object of adequate protection. Further, as the soil surface is usually uneven, mounded parts may not be sufficiently treated with the liquid and, as the result, a uniform film may not be formed on the whole surface of the soil. This results in imperfect moisture and insect resistance and poor wood-preservative effects.

In conventional termite control methods for wooden structures, insect control chemicals containing emulsions or liquid concentrates are sprayed on the under floor soil and on the supporting members for such structures. These methods, however, do not permanently immobilize the insect control chemicals and do not provide prolonged insect control effects because the insect control ingredients evaporate in a relatively short time period. In order to improve permanent immobilization, certain insect control methods have been developed. For instance, in one method a hardened resin foam coated isolation layer containing an insect control chemical is formed by forcefully mixing a main solution (the asphalt emulsion modified polyvinyl acetate resin emulsion, which is a mixture of polyvinyl acetate resin emulsion and asphalt emulsifiable concentrates at about 7:3 proportion) containing an insect control chemical and an organic solvent solution (in which hydrophilic low molecular weight polyurethane resin is dissolved by methyl ethyl ketone or other organic solvents). The mixture is then sprayed on the structure's under floor soil surface.

Asphalt emulsion concentrate is a highly viscous black colored material and asphalt emulsion modified polyvinyl acetate resin is also black. The equipment and tools for spraying this mixture are quickly blackened and dirtied. Operators must be extremely careful when handling and spraying the mixture because their work clothes cannot be cleaned completely if soiled by the mixture. Therefore, work efficiency is significantly reduced. Asphalt emulsion concentrate, because it is usually a cationic surface active agent-based, oil-in-water type emulsion formula, is susceptible to emulsion destruction when in contact with an anionic surface active agent. Therefore, condensation and separation of emulsified-dispersed asphalt can occur. Thus, it significantly restricts the choice of emulsion concentrate used for aqueous polyvinyl acetate resin emulsion. In addition, asphalt is principally composed of hydrocarbons and thus dissolves rubber gaskets and other materials used in the spraying equipment and tools. In addition, polyvinyl acetate emulsion containing added asphalt increases the viscosity of the emulsion, thus making handling more difficult.

The mixed resin foam coating layer formed by mechanically and forcefully mixing the asphalt emulsion modified polyvinyl acetate resin and the organic solvent solution of hydrophilic polyurethane resin and then spraying the resulting formulation embeds and immobilizes the insect control ingredient which is mixed in and sprayed together with the other ingredients. However, the dried coating layer formed thereby gradually contracts over time with the result that an undetermined amount of cracks and gaps appears several years later. The performance of the coating layer at that point is significantly reduced and the insect control effects are greatly diminished.

An object of the present invention is to avoid the defects of the conventional methods as have been described above and as known in the art. Another object of the present invention is to improve the protection of wood materials used in the construction of housing and of wooden structures against moisture, fungi and insect damage.

Another object of this invention is to provide a protective barrier layer that has the flexibility and other properties to prevent cracks in the layer over time, and which is physically stable enough to practically isolate a structure, such as the under floor space of a building from the soil surface over a long time period.

Another object of the invention is to provide an under floor insect control method that has superior operability and easier handling.

A still further object of the invention is to provide a practical and desirable insect control buffer or barrier layer that can keep the insect control chemical ingredients immobilized in a stable condition over a long time period and eliminate chances of termites or other microorganisms eating through and surfacing above the buffer layer.

Yet another object of the present invention is to achieve a superior system for environmental control and protection.

SUMMARY OF THE INVENTION

In achieving the above and other objects, one feature of the present invention relates to a unique barrier that is created from a specially formulated chemical composition.

According to one aspect of the invention, a protective barrier is created between different landscaped areas to control the vegetation to a designated area and prevent invasions of one area by the plant species from the adjoining area.

According to another aspect of the invention, the ground surface in contact with a concrete structure or metal structure is treated or contacted with a liquid containing a selected synthetic resin emulsion to thereby create a protective barrier against attack of the concrete by acid or acid salts in the soil in contact with the concrete.

Yet another aspect of the invention involves forming a layer of barrier film on the surfaces of a tank, pipeline or cable or other structure that is intended to be buried in the ground. Alternatively, the film may be formed on the ground before the structure is installed.

In accordance with another aspect of the invention, the selected resin formulations contain a foaming agent to foam one of the components and to produce a foamed dried film on the ground surface or other surface to be protected, thereby creating a foamed barrier between the ground and the structure, or between different ground areas.

According to still another aspect of the invention, any surface can be treated with a liquid containing a selected synthetic resin emulsion and a suitable control agent such as an anti-fungal or wood-preservative agent, insecticide and/or pesticide, to form a dried film on the exposed surfaces that are exposed to the attack by moisture, fungi, insects, animals and/or vegetation.

A still further aspect of the invention relates to treatment of textile material such as curtains, screens, and drapes with the formulations described herein to impart a variety of properties including insect repellency and moisture control.

According to another aspect of the invention, the ground surface under a house or other structure is treated with a liquid containing a selected synthetic resin emulsion and an anti-fungal and wood-preservative agent and/or a pesticide such as a termite-controlling agent.

In accordance with another aspect of the invention, the selected formulations contain a foaming agent to foam one of the components and to produce a foamed dried film on the ground surface thereby creating a foamed barrier between the ground and the structure.

According to still another aspect of the invention, wood materials for house construction or wooden houses themselves are treated with a liquid containing a selected synthetic resin emulsion and an anti-fungal and wood-preservative agent and/or a pesticide, such as a termite-controlling agent, to form a dried film on the exposed surfaces of wood materials or on the surface of wood houses that are exposed to the attack by moisture, fungi and insects.

In achieving the above and other objects of this invention, applicant has produced various synthetic resin based aqueous emulsions for application to a large number of surfaces to create a barrier layer or protective film to guard against damage or invasion by pests, moisture and fungi as well as other unwanted factors. It has been discovered that a mixed resin foam layer can keep the insect, humidity or fungi control chemical stable and immobilized for a long time period, allows little contraction over time, and effectively prevents cracks even if a slight contraction occurs because of the flexibility of soft to semi hard resins used in the formulation. This layer is formed by spraying, along with, for example, an insect control chemical, a mixture of an aqueous emulsion, which is a copolymeric resin comprised of an acrylic or methacrylic ester based monomer and vinyl acetate (hereinafter referred to as "main solution"), and an organic solvent solution which includes as its primary components a polyurethane resin forming isocyanate and a polyhydroxy compound.

In a particular embodiment of invention, an under floor insect control method for structures is obtained in which an insect control chemical in a mixed resin foam coating can be installed under the floor by forcefully mixing, at a nozzle part of a sprayer, and spraying on the soil surface the following: an aqueous resin emulsion, containing 15–20 percentage by weight solids which is a copolymeric resin, comprising 55 to 85 parts by weight of vinyl acetate and 15 to 45 parts by weight of an alkyl acrylate or alkyl methacrylate or mixtures thereof; an inert organic solvent solution of a mixture of a polyisocyanate and polyalkylene glycol in a proportion ranging from 5–25 and 75–95 parts by weight, respectively, which comprise an adjusted 60–80 percentage by weight as a total volume of the two ingredients; and an insect control chemical. The proportion of organic solvent solution to the aqueous resin emulsion can be in the range of 7–15 percentage by volume.

BRIEF DESCRIPTION OF THE DRAWINGS

The invention will be further understood, with regard to the drawings herein.

DETAILED DESCRIPTION OF THE INVENTION

According to a detailed aspect of the invention, when a selected synthetic resin liquid is applied to the solid surface under a wooden structure, it is essential that it contains a foaming agent. The presence of a foaming agent causes the liquid to be foamed either before, during or after the application of the liquid to the surface. This treatment is normally performed by spraying the synthetic resin liquid on the solid soil surface. However, the composition of the invention can also be sprayed or applied to other surfaces such as metal, cloth, concrete, stone, plaster, stucco, and composite surfaces. When the liquid is sprayed, either as a foam or foamed in situ on the soil surface or during spraying by the action of a foaming agent, the foamed liquid spreads smoothly on the ground surface. This is quite in contrast to the conventional method that employs no foaming agent, according to which, as described above, a large quantity of liquid is required, as it tends to penetrate into the solid rather than spread on top of the soil surface.

Thus, according to the present method, the quantity of the liquid required for the treatment may be reduced compared with prior methods. Further, as the liquid of the invention spreads smoothly on the soil surface, not only the higher parts but also the depressions in the soil surface may be sufficiently covered so as to form an even, dried film. Thus, the treatment can be carried out regardless of the topography of the soil surface.

The method of the invention provides an easy way of working at difference places, such as the ground area under a wooden floor. The treatment with the liquid and the foaming of the composition may readily be performed, for example, by spraying, even after the foundation of the structure has been put in place. Accordingly, the present method may effectively be applied to fully constructed houses around the foundations. The treatment may also be applied under the concrete slab of a house or other building prior to construction of the upper part of the structure. Furthermore, the method of the invention has a practical advantage in that the liquid in a foamed condition is not scattered too much when it is sprayed. This lessens the danger to workers by exposure to the liquid and saves the volume of the liquid required for the treatment.

When the liquid is foamed after application to the soil surface, the situation differs slightly, but similar effects may still be obtained.

According to this mode of treatment, the liquid somewhat penetrates into the soil near the surface. The synthetic resin and the active ingredients contained in the liquid emerge thereafter onto the solid surface as the foaming begins and effectively covers the uneven soil surfaces.

PREFERRED EMBODIMENT OF THE INVENTION

According to one aspect of the present invention, the method is carried out by mixing and spraying an aqueous emulsion of a copolymeric resin as the "main solution" component, with an inert organic solvent solution (hardening agent-based) that contains an isocyanate and a polyhydroxy compound along with an insect control chemical where upon complex reactions of the reactive isocyanate group, water, and the hydroxyl radical occur. The complex reactions form soft to semi hard polyurethane resins while releasing gases within several minutes ranging to several tens of minutes that become the mixed resin foam coating layer in which the insect control chemical or other agent is uniformly dispersed in the main solution component. The method employs the relatively low viscous main solution component and has a superior spraying operability because a relatively small volume of low viscous organic solvent solution (hardening agent-based) is forcefully mixed in at the nozzle part of the sprayer. It is also beneficial, as it does not require operators to worry about soiling themselves.

In one embodiment of the invention, the main solution contains a vinyl acetate copolymer emulsion. A preferred composition is a copolymer of vinyl acetate, 2-ethylhexyl acrylate and vinyl ester of versatic acid. These monomeric components are copolymerized to form a copolymer as described and can be illustrated as follows:

wherein $R_1+R_2+R_3=C^8$. The weight ratio can vary but the ratio of X:Y:Z=6:2:2 has been found to be useful. The symbols n, m and p represent an integer and indicate the number of recurring groups and can vary widely as will be understood by those skilled in the art.

Although the above weight ratio of monomeric components is preferred, the proportions can be varied, usually by 10%.

According to the method of the present invention, an aqueous emulsion of a copolymeric resin as the "main solution" component, with an inert organic solvent solution (hardening agent-based) that contains the polyurethane forming components of an isocyanate and a polyhydroxy compound called the "setting solution", is mixed and sprayed. The aqueous resin emulsion may contain a control substance, such as a herbicide, insecticide, pesticide, filler or the like. Alkaline material such as sodium silicate, sodium or potassium hydroxide may be contained when neutralization with acid is desired.

In another aspect of the invention, the method employs as the main solution, a copolymeric resin emulsion that contains vinyl acetate (VA) and an alkyl acrylate ester or alkyl methacrylic ester (AE), in a proportion ranging from 55–85 and 15–45 parts by weight, respectively. If the VA content is less than 55 parts by weight (AE content is equal to or more than 45 parts by weight), the adhesion to the soil can be reduced and increased proportion of the AE is not beneficial. If the VA component exceeds 85 parts by weight (and the AE content is equal to or less than 15 parts by weight), the layer that is formed tends to be rigid and less flexible, which is not desirable because it can be easily cracked and split by vibration over time. The preferred weight proportion range of VA and AE is 60–80:20–40 and the most desirable is 65–75:25–35.

The AE monomer used to form the above copolymeric resin can be an acrylic or methacrylic acid based alkyl ester, with the alkyl radical containing four carbons or more being more practical. Desirable representative examples of suitable acrylate monomers are n-butyl acrylate and 2-ethylhexyl acrylate; the latter being preferred. In order to improve adhesion to soil, flexibility, tensile strength and other physical properties, a small amount, which is about equal to or less than 30% of total weight VA and AE, of other copolymeric monomers can be incorporated into the copolymeric resin. Such copolymeric monomers include, for example, t-monocarboxylic acid ester group. Other known copolymeric monomers can also be incorporated as long as they do not materially inhibit the functions of the coating layer.

VA-AE based copolymers with a desirable proportion of each of the aforementioned copolymeric monomers are easily formed by a known emulsion polymerization in a water medium. In polymerization, aqueous emulsions with solid content density of 40–50 percentage by weight level are generally obtained. The emulsion can be diluted to an appropriate density, for instances, 15–20 percentage by weight resin solids part, to be used as the main solution in accordance with this invention. In the method, various additives are added to the VA-AE based copolymeric resin emulsion before it is mixed with a hardening agent-based solution. Such additives would be substances known to be useful in forming an under floor insect control soil coating resin foam layer, such as color pigments, anti foaming agents, mold proof agents, viscosity adjusting agents, aromatics, and plasticizers. A relatively small amount of these additives can be selectively incorporated.

Figure 2:
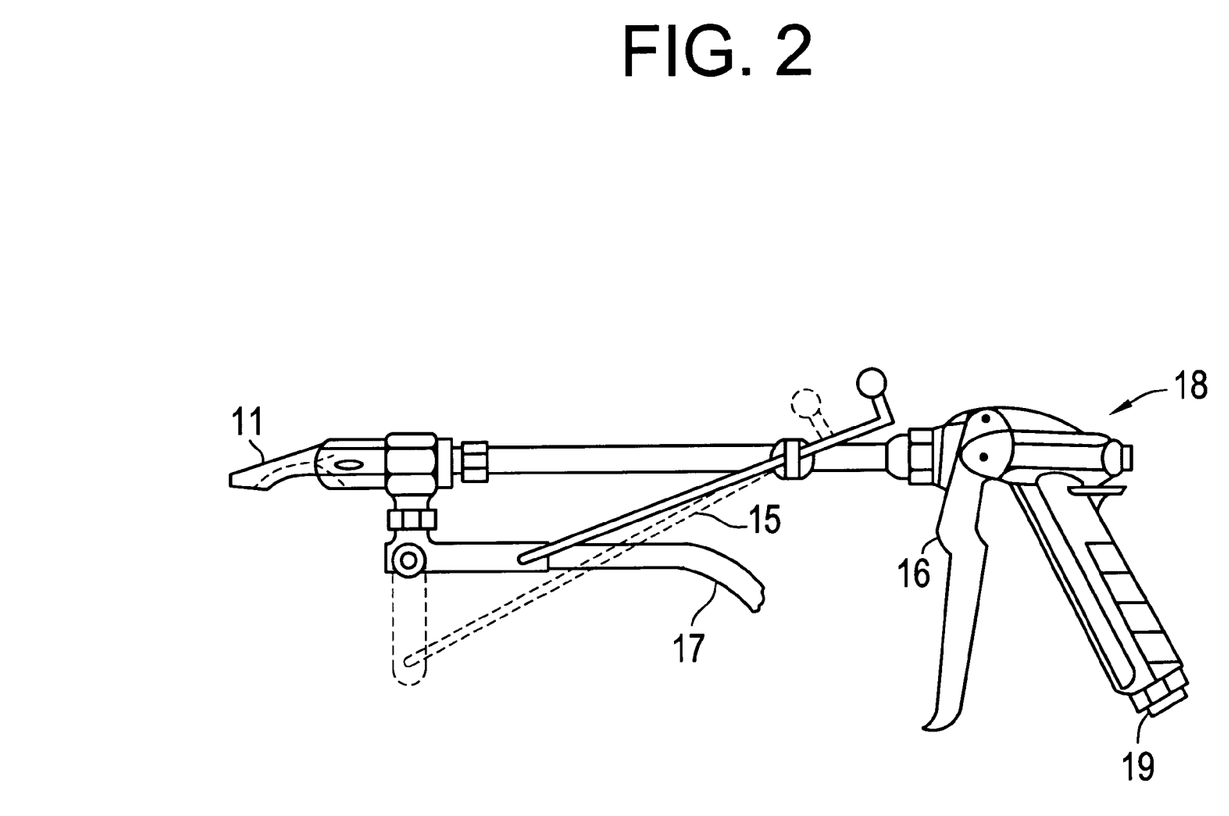
FIG. 2 shows a schematic view of a spray gun used to apply the selected formulation to form the moisture barrier film in accordance with the invention.

In carrying out the present invention, a protective barrier is created by reacting a urethane based resin, as described below, with the above defined synthetic polymer resin emulsion at the nozzle end of a specially designed barrier spraying machine shown in FIG. 2 to form a fast-setting resin film on the surface of soil or under the surface of an inorganic foundation such as cinder block, concrete and the like. Agents such as pesticides and herbicides can be contained in the synthetic resin film. To remain effective for a longer period of time, the film should be formed to be uniformly thick. The accuracy of the spray work can be easily visually judged. So if any thin or defective portion is found in the film, it should be corrected immediately.

The foamed film which is formed after spraying and drying will be sufficiently uniform and thick so as to attain the desired prevention of water evaporation from the solid surface and greatly improve moisture resistance. And, in cooperation with a herbicide and the like, the layer also attains a superior effect against invasion by weeds and biological attacks in general.

Hardening agents used in the method can be non-aqueous solutions in which the isocyanate is preferably a polyisocyanate such as a diisocyanate or triisocyanate and the polyhydroxy compound is preferably a polyalkylene glycol such as polypropylene glycol (PPG) which are dissolved in an inert organic solvent. When mixed with water, isocyanate radicals react completely with the PPG to form a soft to semi-hard foamed polyurethane resin. Appropriate proportion ranges are 5–15 parts by weight the di-or triisocyanate and 85–95 parts by weight PPG. If isocyanate is less than 5 parts by weight (PPG is equal to or more than 95 parts by weight), hardening can take a longer time causing the liquid to dribble, which is not desirable because the thickness of hardened coating layer then becomes inconsistent due to running of the liquid into lower portions of the soil. If the isocyanate exceeds 15 parts by weight (PPG is equal to or less than 85 parts by weight), the reaction speed can be increased and a rigid foam coating can be formed. The desirable proportion of isocyanate and polyhydroxy compound is 10–14:86–90 parts by weight range. The ingredients, proportions and the like conditions can be selected by a person skilled in the art to obtain the current foamed film.

Figure 1:
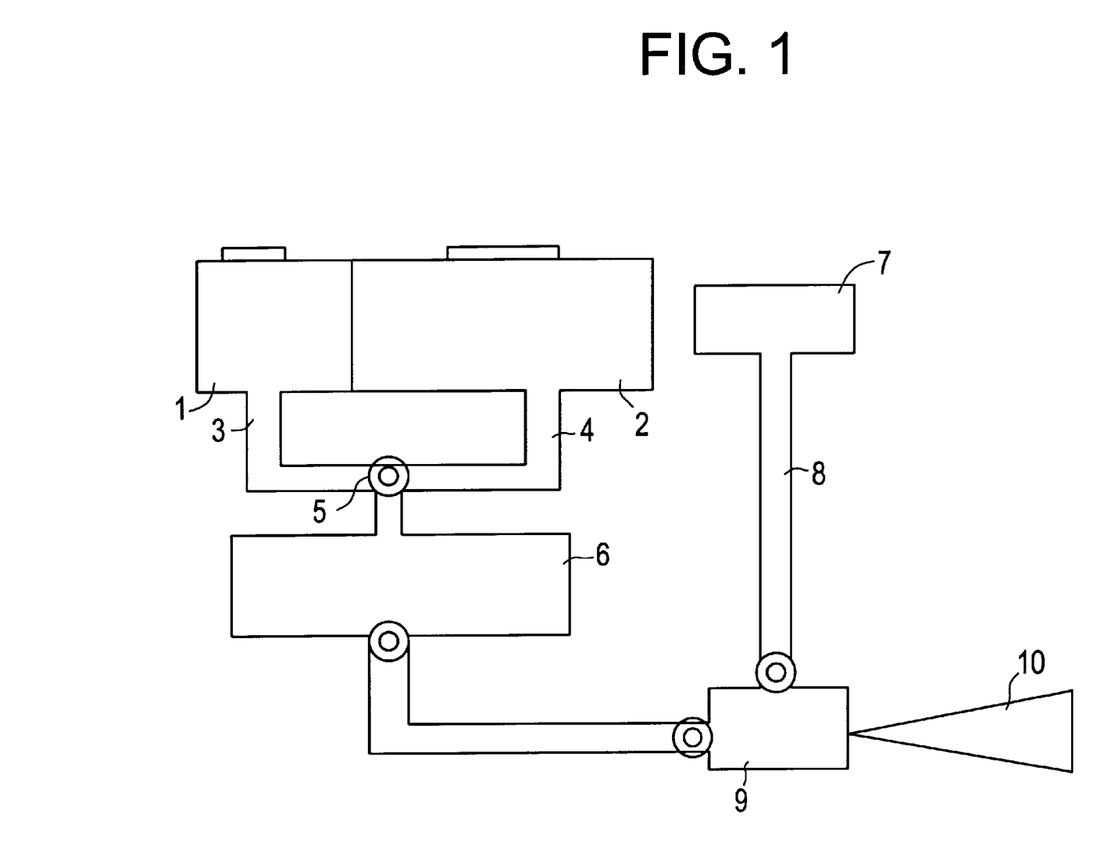
FIG. 1 shows a schematic representation of the spraying system used to practice the invention.

Referring now to FIG. 1, the barrier spraying system of the present invention is schematically illustrated and includes a water tank (1) and a vinyl resin emulsion tank (2) connected with conduits (3) and (4) to metering valve (5) which controls the amounts of water and resin emulsion flowing to the power sprayer (6).

The urethane resin reactant, called the setting agent herein, is conveyed from tank (7) through conduit (8) to the spray nozzle (9). The urethane can be suctioned from this holding tank (7) and flows to join and react with the resin emulsion from vinyl resin emulsion tank (2) at the spray nozzle (9) to form the foam forming barrier spray (10) which is then directed to the surface to be coated.

As mentioned above, the setting component used herein is a foamable polyurethane resin which is of a hydrophilic nature. It is typically made by reacting a polyurethane forming polyisocyanate such as tolylene diisocyanate with an active hydrogen containing polyhydric alcohol such as polypropylene glycol in an inert organic solvent such as butyl lactone and monopropyl ether. However, any suitable isocyanate and polyhydroxy compound known in the art to be capable of producing polyurethane foams can be used herein.

A suitable example of such a material is the commercially available product PUC 165-5-6 which is a light yellow transparent liquid, viscosity of 100–120 cps at 25° C., 1.01–1.04 specific gravity at 25° C., with a non-volatile content of about 70%.

Appropriate isocyanates used in the invention include 2,4-tolylenediisocyanate, 4,4'-diphenylmethane diisocyanate, dianiline diisocyanate, hexamethylene diisocyanate, metaxylene diisocyanate and correspondingly known triisocyanates. These are normally used singularly, but two or more can be selectively combined for applications.

PPG is a condensate of propylene glycol described by the chemical formula of $HO-[CH_2-CH(CH_3)-O]_n-H$, and normally has a relatively low molecular weight ranging around 1000–3000. PPG of the formula above has the number of propylene oxide units (n) in the 20–70 level. If the molecular weight of PPG is too large, it can increase the viscosity of the hardening agent-based organic solvents and may delay the urethane forming reaction, thus it is not always convenient. If the molecular weight of PPG is too low, it reduces the stability of the hardening agent-based solution, thus it is not perfectly desirable either. Appropriate molecular weights may vary slightly depending on the type and amount of isocyanate being mixed in.

Both the isocyanate and PPG, which comprise the hardening agent, are dissolved in chemically nonreactive or inactive organic solvents. Inert organic solvents that can dissolve both ingredients include the ketone solvent group, such as dimethyl ketone, methyl ethyl ketone, and dimethyl ketone, the aliphatic ether solvent group, such as dipropyl ether and methyl propyl ether, the lower aliphatic lactone solvent group such as butyl lactone, and the hydrocarbon solvent group. These inert organic solvents can be used singularly or in combination of two or more. Mixtures of isocyanate and PPG in the aforementioned proportion are dissolved in these organic solvents and the viscosity is adjusted appropriately for applications. Applicable viscosity of such hardening agents, in relation to the total volume of isocyanate and PPG, usually can be within the range of 60–80 percentage by weight.

As described above, the method of the invention may be applied not only to the ground surface but also to the concrete surface, for example the surface of concrete in contact with the ground, metal surfaces, pipelines and cables.

In cases when the method of the invention is directly applied to any of the structural parts described above (hereinafter simply referred to as "structures"), instead of to the soil beneath, at the side of, or surrounding the structure, it is not essential that the liquid contains a foaming agent. That is because the surface of some structures are smooth as opposed to the soil surface which may be rough and uneven.

However, it is preferably that a foaming agent be contained in the liquid and the foaming be performed upon treatment. In these cases too, foaming may be performed either before, during or after the treatment.

As was also the case with the treatment of the soil surface, the timing of foaming may be controlled by the choice of types and amounts of foaming agent and other factors.

When the method of the invention is applied to surfaces, the treatment is normally effected by spraying, although immersion, impregnation and other conventional methods may alternatively be used.

By the method of the invention, the synthetic resin containing liquid reaches well into difficult to access areas. Thus, for example, when the treatment is effected on a soil surface by way of spraying, the liquid can reach even to the uneven surfaces of the soil.

The herbicide and/or vegetation control agent as well as pesticidal agent to be employed in the method of the invention, include, for example, any conventional material capable of performing its intended function when incorporated into the barrier film.

These and other conventional agents, as well as environmentally friendly ingredients, may be employed whether dissolved in a suitable solvent such as water, or in the form of an undiluted oil or liquid.

The quantity of herbicide, vegetation controlling agent, or the like used herein is not critical and will depend on the result intended. A sufficient amount is used to be effective against invasion by undesired plant or animal species including insects. The maximum amount used is purely a matter of economics and is not critical.

The insect control components used in the method are known chemical substances for controlling termites and other insects injurious to wood. These include chlorpyrifos, phoxim: 0,0-dimethyl-0-(α-cyano benzylidene amino) thiophosphate, perhymetholyne: 3 phenoxy benzyl= (IRS.3RS)–(IRS.3RS)-3-(2,2-dichlorovinyl)-2,2-dimethyl cyclopropane carboxylate, ethophenprox: 2-(p-ethoxyphenyl)-2-methylpropyl-3-phenoxy benzyl ether, biphentoline: (2-methyl[1,1-biphenyl]-3-y1)methyl-3-(2-chloro-3,3,3-trifluoro-1-propenyl)-2,2-dimethylcyclopropane carboxylate, silafluophen: (4-ethoxyphenyl)[3-(4-fluoro-3-phenoxyphenyl)propyl] (dimethyl)silane, and pyresroid. Other well known insect control chemicals can be applied, as well.

Two or more of these insect control formulas can be mixed in this application. A single chemical appropriate for a subject insect, however, is normally used for each application. A fixed amount of the chemical is added to the main solution or to the hardening agent-based solution before the two are combined. It is normally added to the main solution; i.e. the copolymeric resin aqueous emulsion. It is important to embed enough concentration of insect control chemical in the protective barrier layer to prevent termites and the like from eating through the layer and entering the under floor space. The appropriate amount depends on the chemical type and the insecticide effects. It is normally within the range of 2–4 percentage by weight of the total weight of the resin mix.

In the method of the invention, the hardening agent solution and the main solution which is the resin emulsion containing the insect control chemical are not truly compatible. It is possible, however, to form a precisely compartmentalized uniform mixture by forcefully and physically mixing them at a nozzle part of a sprayer. The resin solids content concentration of the main solution, for example, the VA-AE copolymerized resin emulsion in this mixture, as stated earlier, is adjusted in the range of 15–20 percentage by volume in consideration of the relatively low viscosity of the hardening agent-base organic solvents and the mixing operability. At the nozzle, the highly viscous solution comprising the hardening agent can be supplied at 7–15 percentages by volume of the aqueous resin emulsion. Too large or too small a percentage can be undesirable because the mixed resin foam may run before hardening or will not obtain relatively appropriate flexibility, hardness, non-contraction property, or physical strength. The preferred range is 8–12 percent by volume.

Before mixing and spraying the mixture, the under floor ground surface must be flattened as much as possible. Normally about 450–600 ml of the main solution emulsion and about 10% by volume of hardening agent in relation to the main solution volume per square meter are sprayed against the ground surface. The sprayed mixture forms soft to semi-hard urethane as the isocyanate radical reacts with emulsion medium and polyhydroxy compound thereby releasing a gas, and hardens to form a foam layer which is comprised of a substantially homogeneous mixed resin with the aforementioned copolymeric resin. The amount of mixture sprayed varies slightly depending on the nature of the soil, such as clay or sand; slightly more for sandy soil. The thickness of the foamed coating layer also varies depending on the soil or foaming condition, but it is applied to form about 1–3 mm thickness when dried.

Forceful mixing of the main solution emulsion and hardening agent-based solution is done instantaneously at a mixing chamber located at a nozzle of a sprayer. The main emulsion, which contains the insect control chemical, is injected in the main pipe of the sprayer by applying pressure and allowing the velocity of the flow to draw hardening agent-based solution from a supplying pipe by utilizing the principle of atomization. The proportion of the mix can be controlled by selecting the feeding speed or the pressure of the main emulsion to the main pipe and adjusting the size of the suction opening for the hardening agent-based solution accordingly. Sprayer equipment described in Japanese Laid-Open Utility Model No. 3-40369 (1991) and Japanese Laid-Open Utility Model No. 4-915 (1992), can be conveniently used as the sprayer that forcefully mixes and sprays the two solutions.

The forcefully mixed solution is ejected from the nozzle by its own force and sprayed essentially uniformly onto the ground surface. The sprayed solution hardens as the isocyanate chemically reacts while releasing a gas, and forms a mixed resin foam coating layer which is substantially homogeneous with the urethane and VA-AE-based copolymer. The coating layer formed in this fashion is a relatively thin resin foam sheet as described above. The layer, however, usually has 80–90% gas barrier property (moisture-proof property) and completely prevents termites and other microorganisms from migrating from soil to under floor space. The layer also substantially prevents moisture in the soil from evaporating, thus effectively preventing wood rot of structural posts and the like. In addition, such resin coating barrier keeps under floor air temperatures cooler in summer and warmer in winter, as compared to the external air. Thus, the foam could be utilized in the air cycle system of the houses and conveniently incorporated during the construction of energy conserving houses.

Hardening speed of the sprayed solution is generally fast if the surrounding temperature is high and slow if the temperature is low. The urethane forming reaction speed can also be controlled by organic solvents in the hardening agent-based solution. Selection and combination of such organic solvents can be easily determined in advance through simple experimentation. Desirable hardening time, judging from on site work conditions, can be usually 15 to 30 minutes after spraying. Work is most efficiently conducted if hardening time in that range is factored in. When forming an insect control layer with this method, the surfaces of columns and beams are preferably treated by a traditional insect control surface treatment immediately before or at the time of spraying. Because the mixed resin foam barrier formed in this invention is thin and light, it can be easily cut with a sharp knife or a cutter and removed if further insect control treatment are necessary.

The insect control mixed resin foam barrier formed by the method of the invention not only embeds insect control ingredients uniformly and in a stable manner, but also functions as a stable insect control gas barrier layer for a long time period because of its appropriate flexibility and non-contraction properties that prevent cracks and gaps.

In forming a protective barrier by reacting a urethane based resin, as described, with the above defined synthetic modified vinyl acetate copolymer resin emulsion containing, for example, an anti-termitic agent, it should be ensured that the completed film does not inhibit the ventilation under the floor so that the film can remain durable in the environment under the floor to sustain the performance of the barrier layer of the invention for a very long period of time.

The isocyanate is used in an amount of up to 25% by weight and the polypropylene glycol is present in an amount of at least 75% by weight. The solvent in the reaction system is about 30% and preferably consists of 15% butyl lactone and 15% monopropyl ether.

Still another advantage of the method of the invention is that a heat-insulation effect may also be brought about as the dried film, which can be made sufficiently thick, contains a multitude of air bubbles as a result of foaming and exerts an insulating effect.

As described above, the method of the invention may be applied not only to the ground surface but also to the wooden parts of houses, and further to wood materials for house construction.

In cases when the method of the invention is directly applied to any of the wooden parts described above (hereinafter simply referred to as "wood") instead of to the soil beneath the wood, it is not essential that the liquid contains a foaming agent. This is because the surface of wood is normally even as compared to the soil surface which may rough and uneven.

However, it is preferable that a foaming agent be contained in the liquid and the foaming be performed upon treatment.

In these cases too, foaming may be performed either before, during or after the treatment.

The following table contains some observations about the reaction conditions to be followed:

| Item | Principal resin emulsion | Setting Agent |
| --- | --- | --- |
| Mixing | To be mixed with an equal quantity of water, and sufficiently stirred, to make a homogeneous diluted solution. | To be used as is. |
| Precautions for mixing | Care should be exercised not to allow any foreign matter to be entrained. Unless the diluted solution is homogeneous a normal film may not be formed. | Care should be exercised not to allow any foreign matter to be entrained. The setting agent should be prevented from being mixed with water, by being kept away form any splash of water. |
| Mixing ratio of clean barrier solution | Diluted principal resin emulsion (vinyl acetate resin emulsion containing the anti-termitic agent). | Setting agent (hydrophilic polyurethane resin) 1. |
| Temperature of Clean Barrier solution. | 3–40° C. (optimum temperatures are 20° C.–30° C.) | |

As was also the case with the treatment of the soil surface, the timing of foaming may be controlled by the choice of types and amounts of foaming agents and other factors.

When the method of the invention is applied to wood, the treatment is normally effected by spraying, although immersion, impregnation and other conventional methods may alternatively be used.

By the method of the invention, the synthetic resin containing liquid reaches well into difficult to access areas such as crevices, knotholes, openings or gaps of joints, particularly when the treatment is performed in the presence of a foaming agent. Thus, for example, when the treatment is effected on a surface of wood by way of spraying, the liquid can reach even to the reverse side of the wood.

The anti-fungal and wood preservative agent and/or pesticidal, termite-controlling agent to be employed in the method of the invention, include, for example, chlordane (normally in the form of an emulsifiable concentrate, water-soluble preparation or oil preparation), mixtures of chlordane and tributyltin compounds, and boron compounds; anti-fungal and wood preservative agents such as penols Nos. 1, 2 or 3 as prescribed by Japanese Industrial Standard (JIS) K 1550, inorganic fluoride compounds, Nos. 1 or 2, chromium, copper or arsine compounds as prescribed by JIS K 1554 and creosote oil as prescribed by JIS K 2439.

These and other conventional pesticides as well as environmentally friendly ingredients may be employed either dissolved in a suitable solvent such as water, or in the form of an undiluted oil or liquid.

The quantity of termitic agent, pesticides or the like used herein is not critical and will depend on likelihood of infestation. A sufficient amount is used to be effective against the insects, fungi, etc. The maximum amount used is purely a matter of economics and is not critical.

The foaming agent to be employed in the method of the invention includes conventional surfactants having the foaming property, preferably anionic surfactants such as fatty acid ether, alkyl sulfates, alkylarylsulfonates (e.g. alkyl-benzenesulfonates) or alkylsuflonates; and isocyanates such as methylenediisocyanate (MDI) and tolylendiisocyanate (YDI). All suitable foaming agents can be used for purposes of this invention.

The amount of foaming agent used is a matter within the scope of a person familiar with urethane technology and can vary as is well known. For a discussion of polyurethane foams and blowing agents, see Kirk-Othmer: Encyclopedia of Chemical Technology, a standard work in the art.

The liquid according to the present invention may contain, if desired, an organic filler such as titanium oxide clay or calcium carbonate, the use of which may bring about a harder dried film. It may also contain a wax emulsion such as paraffin wax emulsion or a silicone resin, the use of which may improve the humidity-resistant property.

A viscosity-increasing agent such a pvoal (polyvinyl acetate), or any additional agent that will promote hardening of the dried film can also be present.

Normally, the liquid is diluted with water, upon treatment, in order to improve the efficiency of work.

The mixing ratio of each component in the liquid will largely vary depending on the various factors, such as conditions of the soil surface under the floor and the type of foaming agent, and the like. Typically, when a surfactant is employed as the foaming agent, it is used in an amount of 1–5 parts, preferably 1–3 parts by weight, based on 100 parts by weight of vinyl acetate emulsion. When an isocyanate is used as the foaming agent, the ratio will not differ very much, and it is normally used in an amount of 1–5 parts by weight, based on 100 parts by weight of vinyl acetate emulsion.

The following is representation of the formulations of this invention.
1) Aqueous emulsion: Solid resin component contains 15–20% by weight of polyvinyl acetate and acrylic component (55–85 parts and 45–15 parts by weight) mixed with
2) Inert organic solvent solution (7–15% by weight of aqueous emulsion (1)) containing 60–80% by weight of diisocyanate and polypropylene glycol (5–15 parts and 95–98 parts by weight).

Other isocyanates and polyhydroxy compounds can be used with comparable results.

In carrying out the invention to prepare and form the protective barrier layer, the apparatus shown in FIG. 1 can conveniently be used. The principal resin emulsion which is based on the vinyl acetate is placed into the principal resin emulsion tank (2) through its inlet. The washing liquid is placed into the washing tank (1) through its inlet. When mixing equal quantities of principal resin emulsion and water, stirring is used for forming a homogenous diluted solution. To use the power sprayer, the change over cocks of the water suction port and the spill port are set to the principal resin emulsion tank side. For washing, the change-over cock of the water solution port is set to the washing tank side. The cock of the principal resin emulsion hose discharge port is then closed, and the motor switch is turned on for starting. The nozzle gun spraying machine is attached to the principal resin emulsion hose discharge port. The principal resin emulsion hose is then extended to the place to be treated. Typically, the pressure is set at 20 kg/cm$^2$ before spraying. The principal resin emulsion hose should be used within a range of about 50 m.

The polyurethane setting agent hose is connected to the setting agent suction port of the nozzle gun spraying machine. If the setting agent hose is attached with insufficient clamping, adequate suction will not be provided. The urethane setting agent hose is at a proper length within 10 m. The urethane setting agent hose (8) is connected to the setting agent tank (7). The nozzle tip is adjusted to keep the clearance between the nozzle control at the end of the nozzle gun of the spraying machine and the nozzle tip in the range of 1 to 3 mm (3 mm when the air temperature is lower than 25° C. and 1 to 2 mm when 25° C. or higher).

If the change-over lever of the nozzle gun of spraying machine is set at the setting agent side, the diluted principal resin emulsion and the setting agent will be ejected simultaneously at a ratio of about 10:1 in parts by weight. Since the setting agent is automatically suctioned by the negative pressure of the principal resin emulsion, the air in the hose up to the nozzle end should be extracted. When the urethane setting agent reaches the nozzle end, the principal resin emulsion is sprayed at a rate of 2.0 to 2.5 kg/m$^2$.

Generally, the ratio of vinyl emulsion to urethane setting agent is 10:0.5 to 10:2, preferably 10:1 parts by weight. The amounts chosen can be varied depending on the results to be achieved and adjustment of proportions is within the skill of the arts.

To halt spraying, the change-over lever of the nozzle gun is set to OFF (air suction) side, and the diluted principal resin emulsion is discharged for several seconds, before halting.

The nozzle gun is used as follows:

The principal resin emulsion hose is attached to the principal resin emulsion joint port (19) of the nozzle gun (18) of the spraying machine.

The urethane setting agent hose (17) is connected to the setting agent suction port. The change-over lever (15) is set at position A shown by the solid line, and the principal resin emulsion control lever (16) is set to eject the diluted principal resin emulsion and the setting agent mixed at a ratio of about 10:1. To halt spraying, the change-over lever (15) is returned to position B shown by the dotted line. The urethane setting agent is automatically suctioned due to the negative pressure of the principal resin emulsion, and it takes about 30 to 40 seconds until the setting agent reaches the nozzle end (11). The power sprayer is set at a pressure of 20 kg/cm$^2{}_1$ and the nozzle gun is connected to the principal resin emulsion, the ejected quantity is adjusted to be in a range from 5.2 to 61/m using a graduated container or meter. The negative pressure gauge is attached to the setting agent hose within 10 m and the hose is connected to the setting agent suction side of the nozzle gun of the spraying machine. The pressure of the power sprayer is then set at 20 kg/cm$^2$, and the principal resin emulsion lever is actuated.

The nozzle tip clearance is adjusted (in a range of 1 to 3 mm) with the negative pressure gauge indication kept in a range from 48 to 62 cm/Hg.

If there is no negative pressure gauge, spray on a trial basis, to measure the decreased quantity of the setting agent, for confirming the ejected quantity.

The invention is further illustrated by the following Examples:

EXAMPLE 1

A liquid preparation is prepared from a vinyl acetate emulsion, a herbicide and a foaming agent (Emal AD-25, Kao-Atlas K.K.). The liquid is sprayed with a spray gun into a trench dug into a ground surface separating a flower bed and the grass area to produce a barrier foamed in situ between the flower bed and the grass area. After spontaneous drying, there is obtained a hardened barrier film.

EXAMPLE 2

The procedures of Example 1 is substantially followed, except that a vinyl acetate emulsion having the non-volatile content of 35% and the viscosity of 100,000 cps is used, to give a dried film. There was obtained a trans-humidity value which was similar to that in Example 1.

EXAMPLE 3

The procedures of Example 1 is substantially followed, except that 3 parts by weight of methylenediisocyanate is used as a foaming agent, giving a hardened film.

EXALPLE 4

The procedure of Example is substantially followed, except that 5% by weight of a paraffin wax emulsion is added to the liquid preparation, affording a hardened film.

EXAMPLES

The following are specific explanations of the invention's termite control method using application examples. In the examples, unless otherwise specified, parts and percentages are those by weight. Also, the moisture-proof ability of the mixed resin foam barrier was measured in accordance with a moisture permeability test method for moisture proof packaging materials used in the JIS (Japan Industrial Standard) Z 0208. The chemical immobilization was determined by analyzing the amount of chemical (density) in the barrier. Flexibility and non-contraction properties were qualitatively determined by observing the existence of cracks.

EXAMPLE 5

A co-polymeric resin aqueous emulsion obtained by emulsifying and co-polymerizing 65% polyvinyl acetate and 35% of equal volume mixture of butyl acrylate and 2-ethyl hexyl acrylate was diluted with water to adjust its resin concentration to 16%. The main solution was prepared by adding 2 kg of chlorphyrifos as an insect control chemical, 3 kg of titanium oxide white pigment containing a small portion of carbon black (gray colored), a small amount of anti-foaming and mold proof agents to 200 kg of the emulsion. The hardening agent-based solution, with 70% hardener, was prepared by dissolving 9% of 2,4 tolylenediisocyanate (TDI) and 91% of PPG in the mixed solvent, in equal volume, of methyl ethyl ketone and gamma-butyl lactone. The main solution and the hardening agent-based solution are forcefully mixed and sprayed by using the equipment described in the Japanese Laid-Open Utility Model No. 3-40369 (1991) onto the under floor soil surface. The sprayer was adjusted to mix the main solution and the hardening agent-based solution at a volume ratio of ten to one. The mixture was sprayed over the ground surface of a wooden house with a floor area of about 30 square meters. The amount sprayed per square meter was 2.5 liters of the main solution and 250 milliliters of the hardening solution.

The sprayed resin mixture layer hardened almost completely in about 15 minutes as the DIC chemically reacted to become a polyurethane foam while emitting a gas. The dried resin foam layer was about 2 mm thick. The insect control chemical component, chlorphrifos, in the layer was measured periodically, from a year after the spraying to eight years after. Annual reduction of the content was equal to or less than 1%. No cracks or gaps were observed in the foam resin insect control layer and no rot or damage of the under floor wood members due to moisture or insects was observed after eight years.

EXAMPLES 6–7 AND COMPARATIVE EXAMPLES 1–4

The main solution emulsion and hardening agent-based solution were prepared as follows:
Preparation of Main Solution Emulsion Four types of main solution aqueous emulsion with different proportions of polyvinyl acetate (VA) and 2-ethyl hexyl acrylate (2EHA) were prepared and the same insect control chemical, pigments, anti-foaming and mold proof agents used in Example 5 were added to each emulsion in the same fashion. Each solution was diluted with water to have a 17% resin solids content. Table 1 shows the weight distribution of each emulsion's copolymeric ingredients.

TABLE 1

| Main Solution Component | Main Component 1 | Main Component 2 | Main Component 3 | Main Component 4 |
|---|---|---|---|---|
| VA | 50 | 60 | 80 | 90 |
| 2EHA | 50 | 40 | 20 | 10 |

Preparation of Hardening Aqent-Based Solution

Three types of hardening agent-based solution (Hardening components 1–3) were prepared by dissolving tolylenediisocyanate (TDI) and polypropylene glycol (PPG) with average molecular weight of 2000 in different proportions into an inactive organic solution comprised of equal volumes of gamma-butyl lactone and methyl propyl ether. Total concentration of the TDI and PPG were adjusted to 70% for each solution. Table 2 shows the weight distribution of TDI and PPG.

TABLE 2

| Hardening Agent-Based Solutions | Hardening Component 1 | Hardening Component 2 | Hardening Component 3 |
|---|---|---|---|
| TDI | 4 | 10 | 16 |
| PPG | 96 | 90 | 84 |

The ground surface was sectioned into a number of one square meter sections. Combinations of main emulsions (Main Component 1–4) and a hardening solution (Hardening Component 2), and a main emulsion (Main Component 2) and hardening solutions (Hardening Components 1–3) were mixed at a proportion of ten (main solution component) to one (hardening solution component) and sprayed on each ground section by using the sprayer used in Example 5 to obtain a mixed resin foam layer that adhered to the ground. Each foam layer after drying was about 2 mm thick. The insect control chemical's immobilization property, the moisture proof property and the existence of cracks were determined. Table 3 shows the combinations of the main emulsion and hardening solution for each example.

TABLE 3

|  | CE 1 | EX 6 | EX 7 | CE 2 | CE 3 | CE 4 |
|---|---|---|---|---|---|---|
| Main Solution | 1 | 2 | 3 | 4 | 2 | 2 |
| Hardening | 2 | 2 | 2 | 2 | 1 | 3 |

In each combination, the reduction of insect control chemical was less than several percentages after five years and the insect control chemical was satisfactorily immobilized. Comparative Example 1 was not so desirable because of a slight inferiority in adhesion to soil and cost of materials. Comparative Example 2's resin barrier was somewhat too hard, not so flexible enough as desired, and caused some cracks over time. Comparative Example 3 did not foam sufficiently and hardened slowly, causing the solution to run. Thus, it did not provide stable or high gas barrier property as desired because the thickness was somewhat inconsistent. Comparative Example 4 was relatively susceptible to deterioration from ultraviolet light, thus had some problems in the weatherproofing aspect. Barriers formed in Examples 6 and 7 did not have such problems described above and the barriers functioned as stable insect control layers for a long time period.

EXAMPLE 8, COMPARATIVE EXAMPLES 5, 6

Using the aforementioned Hardening Component 2 and Main Component 2, the valve on the hardening agent-based solution suction pipe side of the sprayer was adjusted to vary the mixture proportions to form a mixed resin foam layer on the ground sections. Table 4 shows the distribution of mixed resin for each example.

TABLE 4

|  | CE 5 | EX 6 | CE 6 |
|---|---|---|---|
| Main Component 2 | 100 | 100 | 100 |
| Hardening Component 2 | 5 | 10 | 20 |

Comparative Example 5's hardening speed was slower, causing somewhat insufficient foaming and the solution ran into low portions of valleys on the soil surface. The layer thickness was relatively inconsistent and did not provide a perfectly desirable gas barrier. Comparative Example 6 had more urethane resin foam than necessary and was relatively susceptible to deterioration from ultraviolet light. It needed to be replaced in a relatively short time period because it was not desirably stable over time.

The mixed resin foam insect control barrier formed by the method of the invention provides superior insect control chemical immobilization, gas barrier and crack proof properties. It prevents termites and other microorganisms in the ground from encroaching into the under floor space and also prevents moisture from permeating. The method safely maintains wooden residential structures over a prolonged time period.

EXAMPLE 9

A liquid preparation was prepared from a vinyl acetate emulsion, a termite-controlling agent (80% chlordane emulsifiable concentrate diluted with water to 20 times weight), and a foaming agent (Emal AD-25, Kao-Atlas K.K.). The liquid was sprayed onto a ground surface under the floor of a wooden structure with a spray gun in two ways; the one that was foamed in situ, and another that had been foamed previously with a stirrer. After a spontaneous drying, there was obtained a hardened film having the thickness of $500\mu$, which was tested for moisture permeability according to the method as prescribed by JIS Z 0208 (Cup method), which result showed the value 282.0 $g/m^2$0.24 hours.

It is known that the moisture permeability for a Japanese paper (which corresponds to a control where no hardened film is formed on the ground surface) is 994.7 $g/m^2$0.24hours and, from the comparison of the figures, it is clearly shown that a superior moisture-resistant effect is obtained by the method of the invention.

EXAMPLE 10

The procedures of Example 9 were substantially followed, except that a vinyl acetate emulsion having the non-volatile content of 35% and the viscosity of 100,000 cps was used, to give a dried film. There was obtained a trans-humidity value which was similar to that in Example 9.

EXAMPLE 11

The procedures of Example 9 were substantially followed, except that an emulsifiable concentrate containing 80% chlordane and 12% 4-chlorophenyl-3-iodopropargylformal (wood-preservative agent) was used, affording a hardened film.

EXAMPLE 12

The procedures of Example 9 were substantially followed, except that 3 parts by weight of methylenediisocyanate was used as a foaming agent, giving a hardened film.

EXAMPLE 13

The procedures of Example 9 were substantially followed, except that 5% by weight of a paraffin wax emulsion was added to the liquid preparation, affording a hardened film.

The spray work procedure to carry out the present invention can be carried out as follows:

The principal resin emulsion and urethane setting agent for the barrier spray work is generally diluted by an equal quantity of water to form a diluted emulsion. The urethane setting agent is used as is. Then the area to be sprayed is measured, for deciding the quantity to be sprayed. The quantity of diluted principal resin emulsion can be calculated as:

=Area to be sprayed $(m^2)$×Quantity to be sprayed (kg)

=Quantity of diluted principal resin emulsion (kg)/2

The diluted principal resin emulsion is prepared by mixing 1 part of principal resin emulsion and 1 part of water.

Example: For spraying an area of 100$m^2$ with the diluted principal resin emulsion at 2 kg/$m^2$:

Quantity of diluted principal resin emulsion=100$m^2$×2 kg=200 kg

Quantity of principal resin emulsion=200 kg/2=100 kg.

The nozzle gun of the spraying machine is adjusted to keep the ratio of diluted principal resin emulsion to setting agent at 10:1.

Quantity of setting agent used (kg)=Area to be sprayed $(m^2)$×Quantity to be sprayed (kg)/10.

Example: For spraying an area of 100 $m^2$ with the diluted principal resin emulsion at 2 kg/$M^2$:

Quantity of setting agent used=(100 m²×2 kg)/10=20 kg.

Before applying to the soil, the soil to be sprayed is cleaned by removing all the residual materials, debris, and trash from under the floor. Then the soil is leveled using a rake, lay-out tool, land grading machine, etc. If the ground surface is very rough, high portions are cut to fill low portions with the cut soil, for leveling.

If a stone or debris, etc. protrudes above the soil surface, it is pressed from above, to bury it into the soil, or removed by digging and filling the dug hole with soil. If the soil surface is dry, it is recommended to sprinkle a small quantity of water, for wetting the soil surface, before leveling.

The nozzle end is kept away from the ground surface by about 40 to 50 cm, when spraying to prevent the same from being blown up by the discharge pressure in the case of sandy soil.

For clay type soil, ordinary spray work can be adopted. However, when the soil is fissured by drying, the soil should be compacted by rolling. In the case of fine gravel, leveling with rolling compaction is recommended. In the case of coarse gravel, it should be leveled at first, and re-leveled while filling the gravel gaps with sand under rolling compaction.

With the spraying machine having the nozzle gun attached, the nozzle lever is set to ON (setting agent side), and the diluted principal resin emulsion is ejected from the nozzle end into a polyethylene container or oil can, etc. without mixing with the setting agent, for extracting the air in the setting agent hose.

The spray work for a new building should be executed when floor joists have been attached to the entire floor framing.

For spraying under the floor of an existing building, spraying should be started from the deepest portion under the floor to ensure that the operator never moves over the sprayed portions. When the spray work is executed twice for a new building, it is sprayed thinly at first to an extent that the surface soil is visible through the thin film, and then sprayed a second time for finishing.

Care should be exercised not to damage the film especially immediately after completion of spray work. Therefore, portions sprayed with the solution should not be disturbed for 1 to 2 days after completion of spray work.

Further variations and modifications of the foregoing will be apparent to those skilled in the art from the foregoing and are intended to be encompassed by the claims appended hereto.

What is claimed is:

1. A method for creating a protective barrier coating on a surface comprising:

mixing an aqueous emulsion of a copolymer of
 vinyl acetate,
 2-ethylhexyl acrylate and
 a vinyl ester of versatic acid
with an inert organic solvent solution of an isocyanate and polyhydroxy compound to form a reaction mixture and
applying said reaction mixture to said surface under conditions to cause foaming of said isocyanate and polyhydroxy compound and thereby forming an adherent foamed resin layer on said surface.

2. The method according to claim 1, wherein said surface is soil.

3. The method according to claim 1, wherein said surface is concrete.

4. The method according to claim 1, wherein said surface is metal.

5. The method according to claim 1, wherein said surface is a pipe or cable.

6. The method according to claim 1, wherein said surface is a textile.

7. The method according to claim 1, further comprising mixing an insecticide, or herbicide, into said coating.

8. A method for creating a protective barrier coating on a surface comprising:

mixing an aqueous emulsion of a copolymer of polyvinyl acetate and an acrylic ester with an inert organic solvent solution of an isocyanate and polyhydroxy compound to form a reaction mixture and applying said reaction mixture to said surface under conditions to cause foaming of said isocyanate and polyhydroxy compound and thereby forming an adherent foamed resin layer on said surface.

9. A two-component composition for creating a protective barrier coating on a surface comprising:

(a) an aqueous emulsion of a copolymer of vinyl acetate, 2-ethylhexyl acrylate and a vinyl ester of versatic acid, and optionally an insecticide or herbicide, and (b) an inert organic solvent solution of a polyurethane forming admixture of an isocyanate and polyhydroxy compound.

10. A two-component composition for creating a protective barrier coating on a surface comprising:

(a) an aqueous emulsion of a copolymer of polyvinyl acetate and an acrylic ester, and optionally an insecticide or herbicide, (b) an inert organic solvent solution of a polyurethane forming admixture of an isocyanate and polyhydroxy compound.

11. An insect control method for structures comprising:

(1) preparing (a) an insect control agent, (b) an aqueous emulsion, of which 15–20 percentage by weight is a solid resin component of a copolymeric resin containing polyvinyl acetate and alkyl methacrylate at a proportion ranging from 55–85 and 15–45 parts by weight, respectively, (c) an inert organic solvent solution containing a mixture of an isocyanate and polyhydroxy compound at a proportion ranging from 5–15 and 85–95 parts by weight, respectively, which comprises an adjusted 60–80 percentage by weight as a total volume of the isocyanate and the polyhydroxy compound;

(2) forcefully mixing the insect control agent, the aqueous emulsion and the inert organic solvent solution to form a mixture; and (3) forming an insect control chemical in a mixed resin foam coating which is installed under said structure.

12. The method according to claim 11, wherein the proportion of the inert organic solvent solution to the aqueous emulsion is in the range of 7–15 percentage by volume.

13. The method according to claim 11, wherein the alkyl methacrylate is butyl acrylate, 2-ethylhexyl acrylate or a combination thereof.

14. The method according to claim 11, wherein said resin is a copolymer of:

(X)

vinyl acetate

-continued 2-ethylhexyl acrylate (Y)

vinyl ester of versatic acid (Z)

wherein $R_1+R_2+R_3=C_8$; and n, m and p are whole numbers and represent the number of recurring groups.

15. The method according to claim 14, wherein X:Y:Z= 6:2:2.

16. The method according to claim 11, wherein the emulsion further contains a foaming agent.

17. The method according to claims 16, wherein the foaming is effected, before, during or after said forming step.

18. The method according to claim 16, wherein the foaming agent is a surfactant or an isocyanate compound.

19. The method according to claim 18, wherein said surfactant is an anionic surfactant.

20. The method according to claim 18, wherein the isocyanate compound is a diisocyanate or triisocyanate.

21. The method according to claim 16, wherein the pesticide is a termite-controlling agent.

22. The method according to claim 16, wherein one or more of the liquids further contains paraffin wax.

23. The method according to claim 16, wherein the forming is effected on the ground surface under the floor of a building having a floor.

24. The method according to claim 11, further comprising foaming the said mixture and spraying on said wood or ground surface.

25. A method for protecting a wooden surface against attack by pests, humidity or fungi comprising:

(1) preparing (a) a pesticide, moisture or fungi control agent, (b) an aqueous emulsion, of which 15–20 percentage by weight solids is a copolymeric resin of 55–85 parts by weight vinyl acetate and 15–45 parts by weight alkyl methacrylate, (c) an inert organic solvent solution containing a mixture of from 5–15 parts by weight an isocyanate and 85–95 parts by weight polyhydroxy compound, which comprises an adjusted 60–80 percentage by weight as a total volume of the isocyanate and the polyhydroxy compound, (2) forcefully mixing the pesticide, moisture or fungi control agent, the aqueous emulsion and the inert organic solvent solution to form a mixture; and (3) forming a protective barrier on said wooden surface or on a surface in contact with said wooden surface or on a surface in the proximity of said wooden surface from which pests, moisture of fungi would migrate to said wooden surface.

26. The method according to claim 25, wherein said resin is a copolymer of:

vinyl acetate (X)

2-ethylhexyl acrylate (Y)

* * * * *